(12) United States Patent
Brown

(10) Patent No.: US 7,530,967 B2
(45) Date of Patent: May 12, 2009

(54) POROUS MULTIPLE SAMPLE SLEEVE AND BLOOD DRAWING DEVICE FOR FLASH DETECTION

(75) Inventor: Leroy Brown, Orangevale, CA (US)

(73) Assignee: ClearView Patient Safety Technologies, LLC, Haiku, HI (US)

( * ) Notice: Subject to any disclaimer, the term of this patent is extended or adjusted under 35 U.S.C. 154(b) by 683 days.

(21) Appl. No.: 10/836,231

(22) Filed: May 3, 2004

(65) Prior Publication Data

US 2005/0245870 A1 Nov. 3, 2005

(51) Int. Cl.
A61M 1/00 (2006.01)
A61B 5/00 (2006.01)
B65D 81/00 (2006.01)

(52) U.S. Cl. .................. 604/122; 604/403; 600/576

(58) Field of Classification Search ............. 604/122, 604/403, 264, 404, 407, 181, 411–416, 187, 604/93.01, 263, 192–198; 600/573–584
See application file for complete search history.

(56) References Cited

U.S. PATENT DOCUMENTS

| 3,382,865 | A | 5/1968 | Worrall, Jr. |
| 3,469,572 | A | 9/1969 | Nehring |
| 3,585,984 | A | 6/1971 | Buchanan |
| 3,664,879 | A | 5/1972 | Olsson |
| 3,817,240 | A | 6/1974 | Ayres |
| 3,874,367 | A | 4/1975 | Ayres |
| 3,877,465 | A | 4/1975 | Miyake |
| 3,886,930 | A | 6/1975 | Ryan |
| 4,106,497 | A | 8/1978 | Percarpio |
| 4,108,175 | A | 8/1978 | Orton |
| 4,140,108 | A | 2/1979 | Nugent |
| 4,154,229 | A | 5/1979 | Nugent |
| 4,166,450 | A | 9/1979 | Abramson |
| 4,193,400 | A | 3/1980 | Loveless et al. |
| 4,207,870 | A | 6/1980 | Eldridge |

(Continued)

FOREIGN PATENT DOCUMENTS

JP 2001 056527 9/2002

(Continued)

*Primary Examiner*—Matthew F Desanto
(74) *Attorney, Agent, or Firm*—David R. Yohannan; Kelley Drye & Warren LLP

(57) ABSTRACT

A device for drawing fluid from a lumen, and particularly blood from a blood vessel, is disclosed. The device may provide indication of the entry of an intravenous cannula into the lumen. The device may include a central body having an outer wall and an inner fluid passage. The device may include a luer-type adapter to permit the attachment of an I.V. infusion set of various lengths ("butterfly needle") and or any luer-type fitting attached to an existing device. The outer wall of the central body may be transparent or translucent to permit the detection of fluid within the inner fluid passage. A front cannula may extend from one end of the central body and a rear cannula may extend from the other end of the central body. Both the front and rear cannulae may communicate with the inner fluid passage. An air-permeable flexible sleeve may surround at least a tip portion of the rear cannula. The air-permeable flexible sleeve may act as a venting member positioned between the rear cannula and the ambient. The venting member may permit the passage of air through it, but be substantially impermeable to liquids, such as blood.

4 Claims, 7 Drawing Sheets

U.S. PATENT DOCUMENTS

| | | | |
|---|---|---|---|
| 4,269,186 A | | 5/1981 | Loveless et al. |
| 4,296,759 A | | 10/1981 | Joslin et al. |
| 4,307,731 A | | 12/1981 | Kaufman |
| 4,312,362 A | | 1/1982 | Kaufman |
| 4,317,445 A | | 3/1982 | Robinson |
| 4,317,456 A | | 3/1982 | Percarpio |
| 4,326,541 A | | 4/1982 | Eckels |
| 4,340,068 A | | 7/1982 | Kaufman |
| 4,398,544 A | * | 8/1983 | Nugent et al. ............... 600/576 |
| 4,409,990 A | | 10/1983 | Mileikowsky |
| 4,412,548 A | | 11/1983 | Hoch |
| 4,416,290 A | | 11/1983 | Lutkowski |
| 4,416,291 A | | 11/1983 | Kaufman |
| 4,418,703 A | | 12/1983 | Hoch et al. |
| 4,436,098 A | | 3/1984 | Kaufman |
| 4,444,203 A | | 4/1984 | Engelman |
| 4,679,571 A | | 7/1987 | Frankel et al. |
| 4,788,986 A | | 12/1988 | Harris |
| 4,834,707 A | * | 5/1989 | Evans ......................... 604/122 |
| 4,841,985 A | | 6/1989 | Wanamaker |
| 4,844,089 A | | 7/1989 | Roberti |
| 4,865,592 A | | 9/1989 | Rycroft |
| 4,886,072 A | | 12/1989 | Percarpio et al. |
| 4,894,052 A | | 1/1990 | Crawford |
| 4,964,854 A | | 10/1990 | Luther |
| 4,971,068 A | | 11/1990 | Sahi |
| 4,972,843 A | | 11/1990 | Broden |
| 5,030,207 A | | 7/1991 | Mersch et al. |
| 5,032,116 A | | 7/1991 | Peterson et al. |
| 5,033,476 A | | 7/1991 | Kasai |
| 5,069,225 A | | 12/1991 | Okamura |
| 5,086,780 A | | 2/1992 | Schmitt |
| 5,090,420 A | | 2/1992 | Nielsen |
| 5,092,845 A | | 3/1992 | Chang |
| 5,112,327 A | | 5/1992 | Iinuma et al. |
| 5,120,317 A | | 6/1992 | Luther |
| 5,120,319 A | | 6/1992 | Van Heugten et al. |
| 5,122,121 A | | 6/1992 | Sos et al. |
| 5,133,362 A | | 7/1992 | Moss |
| 5,137,518 A | | 8/1992 | Mersch |
| 5,181,523 A | | 1/1993 | Wendelborn |
| 5,201,794 A | | 4/1993 | Kasai et al. |
| 5,217,025 A | | 6/1993 | Okamura |
| 5,222,502 A | | 6/1993 | Kurose |
| 5,242,411 A | | 9/1993 | Yamamoto et al. |
| 5,259,392 A | | 11/1993 | Schmitt |
| 5,273,540 A | | 12/1993 | Luther et al. |
| 5,290,246 A | | 3/1994 | Yamamoto et al. |
| 5,295,969 A | | 3/1994 | Fischell et al. |
| 5,303,713 A | | 4/1994 | Kurose |
| 5,306,259 A | | 4/1994 | Fischell et al. |
| 5,450,856 A | | 9/1995 | Norris |
| 5,496,281 A | | 3/1996 | Krebs |
| 5,520,193 A | | 5/1996 | Suzuki et al. |
| 5,531,701 A | | 7/1996 | Luther |
| 5,533,988 A | | 7/1996 | Dickerson et al. |
| 5,542,932 A | | 8/1996 | Daugherty |
| 5,683,370 A | | 11/1997 | Luther et al. |
| 5,685,860 A | * | 11/1997 | Chang et al. ................. 604/192 |
| 5,697,914 A | | 12/1997 | Brimhall |
| 5,755,701 A | | 5/1998 | Sarstedt |
| 5,830,190 A | | 11/1998 | Howell |
| 5,885,251 A | | 3/1999 | Luther |
| 5,893,844 A | | 4/1999 | Misawa |
| 5,913,848 A | | 6/1999 | Luther et al. |
| 5,916,208 A | | 6/1999 | Luther et al. |
| 5,957,893 A | | 9/1999 | Luther et al. |
| 5,984,895 A | | 11/1999 | Padilla et al. |
| 6,004,278 A | * | 12/1999 | Botich et al. ................. 600/576 |
| 6,096,006 A | | 8/2000 | Sarstedt et al. |
| 6,110,160 A | | 8/2000 | Farber |
| 6,156,010 A | | 12/2000 | Kuracina et al. |
| 6,190,370 B1 | | 2/2001 | Tsui |
| 6,238,371 B1 | * | 5/2001 | Himbert et al. ............. 604/187 |
| 6,261,263 B1 | | 7/2001 | Huet et al. |
| 6,500,157 B2 | | 12/2002 | Luther |
| 6,533,760 B2 | | 3/2003 | Leong |
| 6,595,954 B1 | | 7/2003 | Luther et al. |
| 6,616,637 B2 | * | 9/2003 | Alexander et al. .......... 604/192 |
| 6,712,792 B2 | | 3/2004 | Leong |
| 6,863,662 B2 | | 3/2005 | Luther |
| 2002/0004647 A1 | | 1/2002 | Leong |
| 2003/0078544 A1 | | 4/2003 | Chen |
| 2003/0105414 A1 | | 6/2003 | Leong |
| 2003/0229315 A1 | | 12/2003 | Leong et al. |
| 2004/0143226 A1 | * | 7/2004 | Marsden ..................... 604/272 |

FOREIGN PATENT DOCUMENTS

| | | |
|---|---|---|
| JP | 2002 253535 | 9/2002 |
| JP | 3674946 B2 | 9/2002 |
| JP | 2002-253535 * | 10/2002 |
| WO | WO 99/23947 | 5/1999 |

* cited by examiner

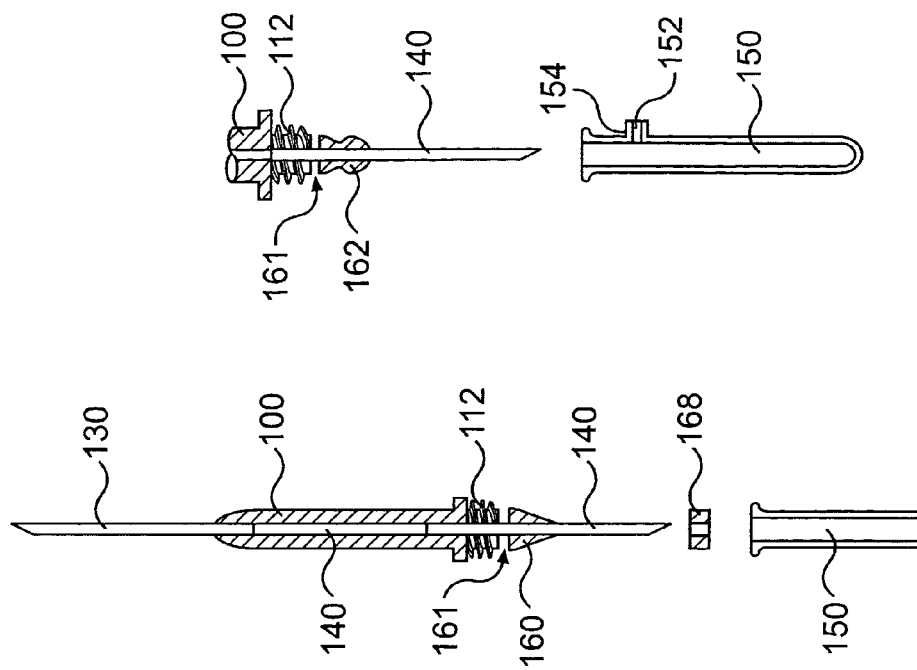
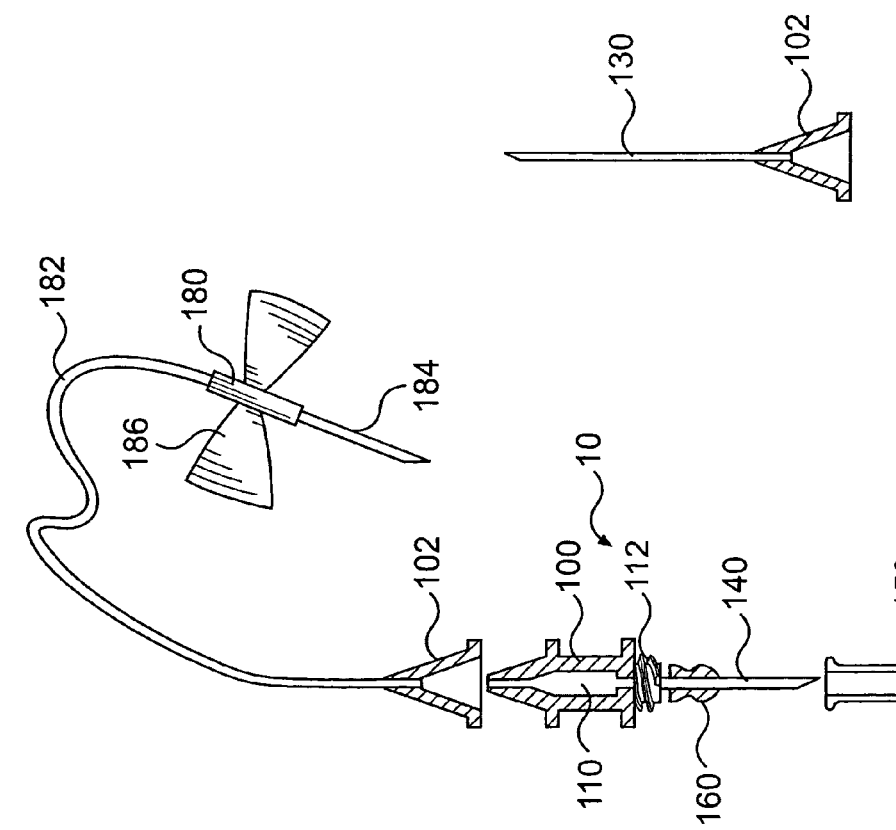

POROUS MULTIPLE SAMPLE SLEEVE AND BLOOD DRAWING DEVICE FOR FLASH DETECTION

FIELD OF THE INVENTION

The present invention relates to a multiple sample sleeve and apparatus for drawing bodily fluids, and particularly blood, from an animal.

BACKGROUND OF THE INVENTION

Intravenous blood collection assemblies have long been used to draw bodily fluids, such as blood, from patients. With respect to drawing blood in particular, the vessel or lumen from which the blood is drawn is often rather small and or not visible. If the needle tip is not in communication with the interior of the blood vessel during the procedure, the procedure is likely to be unsuccessful, causing error, undermining the integrity of the specimen, and the patient may be harmed additionally by the penetration of delicate underlying structures. Accordingly, confirmation of accurate placement of the needle tip into a blood vessel is desirable for blood drawing procedures.

Past intravenous blood collection assemblies have included mechanisms for indicating when a needle tip is in communication with the interior of a blood vessel. These needle kits have included a transparent portion in the needle body from which the presence of blood can be observed. The observation of blood in the needle body is known as "flash." Flash detection has been less than satisfactory for many such collection assemblies. In some instances, the flow of blood into the transparent portion of the needle body is impeded by air backpressure in the needle, and thus flash confirmation is not visible or delayed. This delay can impede the determination of the precise moment at which the needle tip enters the blood vessel, which may cause the healthcare worker inserting the needle to miss or perforate the vessel and penetrate into delicate surrounding structures. In other instances, while flash occurs, the visual indication of flash is not easily detected because the amount of flash is small or obscured due to the positioning of the collection assembly. Accordingly, there is a need for a blood-drawing device that provides flash relatively rapidly and to an extent that a user may readily detect it.

SUMMARY OF THE INVENTION

Responsive to the foregoing challenges, Applicant has developed an innovative device for drawing fluid from a lumen, comprising: a central body having an outer wall and an inner fluid passage; a front cannula communicating with the inner fluid passage; a rear cannula communicating with the inner fluid passage; and an air-permeable flexible sleeve surrounding at least a tip portion of the rear cannula.

Applicant has further developed an innovative method of drawing blood from a lumen comprising the steps of: providing a blood drawing device including a rear cannula surrounded by an air-permeable flexible sleeve; inserting the blood drawing device into a lumen; receiving blood into the blood drawing device; and venting air through the air-permeable flexible sleeve responsive to the receipt of blood in the device.

Applicant has further developed an innovative flexible sleeve adapted to receive a cannula, said sleeve comprising: an open end, a closed end, and an air-permeable wall.

Applicant has still further developed an innovative method of making an air-permeable flexible sleeve, comprising the steps of: providing a hydrophobic matrix material; mixing the hydrophobic matrix material with a hydrophilic porous agent; forming a flexible sleeve from the mixture of hydrophobic matrix material and hydrophilic porous agent; and drying the mixture of hydrophilic porous agent sufficiently to render the flexible sleeve air-permeable.

It is to be understood that both the foregoing general description and the following detailed description are exemplary and explanatory only, and are not restrictive of the invention as claimed.

BRIEF DESCRIPTION OF THE DRAWINGS

In order to assist the understanding of this invention, reference will now be made to the appended drawings, in which like reference characters refer to like elements.

FIG. 5A is a side view in cross-section of a second embodiment of the present invention incorporated into a Luer-type blood drawing device in combination with a standard hypodermic needle or I.V. infusion set ("butterfly needle").

FIG. 5B is a side view in cross-section of an alternative Luer-type hub for use with the Luer-type blood drawing device shown in FIG. 5A.

FIG. 6 is a side view in cross-section of a third embodiment of the present invention.

FIG. 7 is a side view in cross-section of the rear cannula portion of a fourth embodiment of the present invention.

DETAILED DESCRIPTION OF EMBODIMENTS OF THE INVENTION

Figure 1:
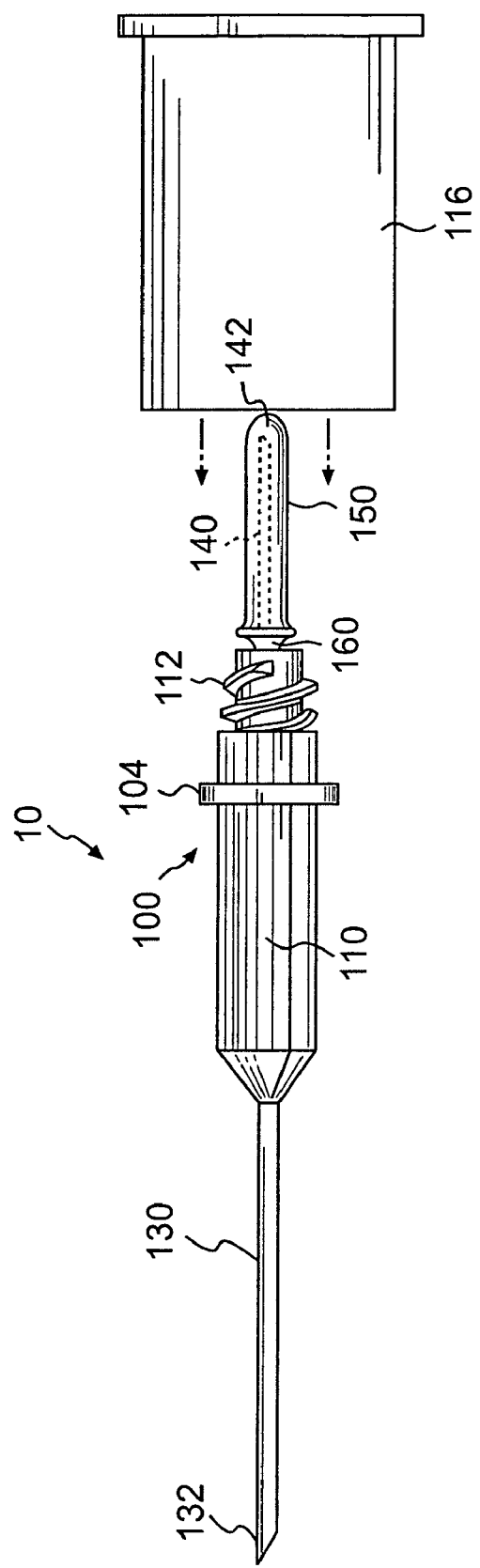
FIG. 1 is an exploded pictorial side view of a first embodiment of the present invention.

Reference will now be made in detail to a first embodiment of the present invention, an example of which is illustrated in the accompanying drawings. With reference to FIG. 1, an exploded pictorial view of a blood-drawing device 10 is shown. The blood-drawing device 10 includes a front cannula 130, a central body 100, a venting member 160, a rear cannula 140, and a flexible sleeve 150. A guide tube 116 may be connected to the central body 100. The front cannula 130 and the rear cannula 140 may each have a generally elongated cylindrical body defining an elongated fluid passage extending from one end of the cannula to the other end. The front cannula 130 may extend from the front end of the central body 100 and terminate at a tapered or pointed end 132, which is adapted to be inserted into a lumen. The rear cannula 140 may extend from the rear of the central body 100 and terminate at a tapered or pointed end 142. The sleeve 150 may isolate the rear cannula 140 from the ambient, wherein the ambient includes any space outside of the sleeve 150, irrespective of whether or not the space is contained within the guide tube 116 or any other structure.

Figure 2:
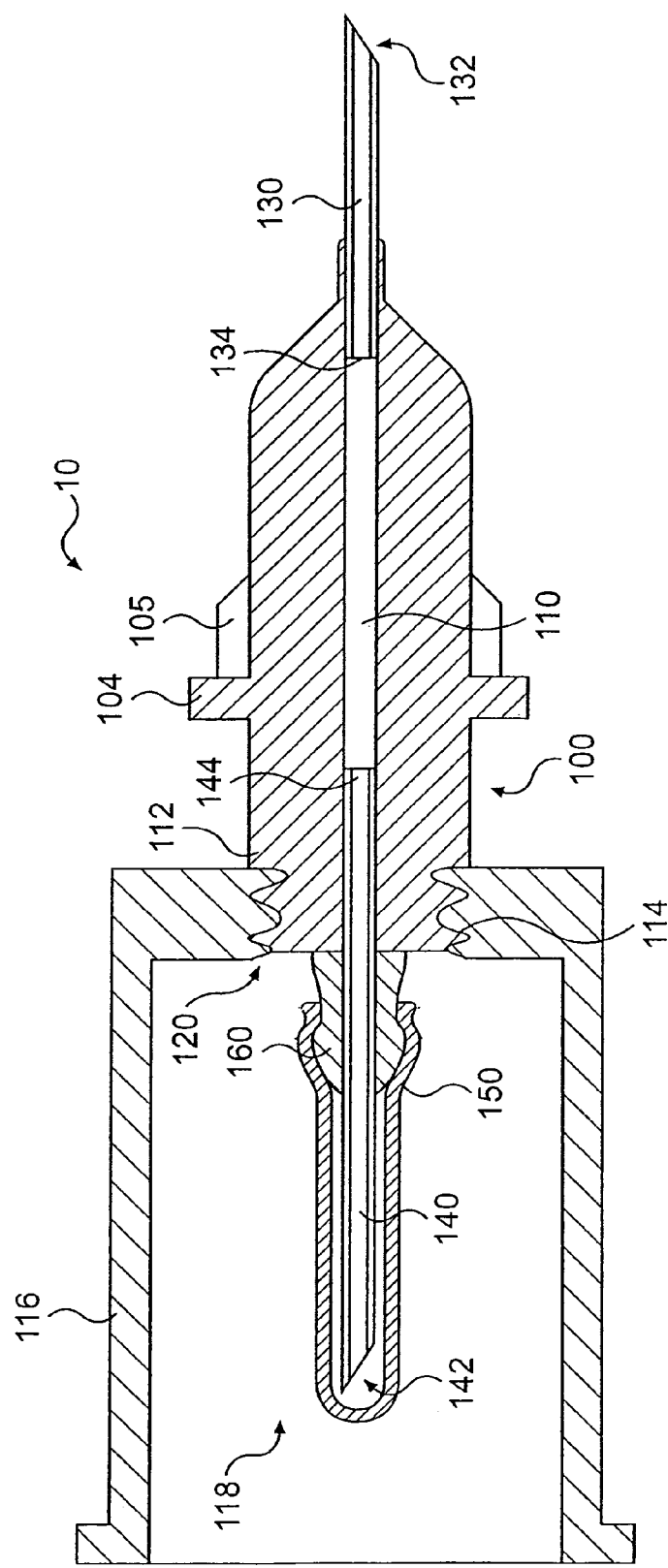
FIG. 2 is a side view in cross-section of the first embodiment of the present invention prior to the insertion of a sample collection tube.

With reference to FIGS. 1 and 2, the central body 100 may include one or more constituent elements, such as a threaded connector 112, which may be integrally formed with, or connected to the central body using adhesive, male-female interfaces, threaded interfaces, or any other connection means. The central body 100 may include an annular ring 104, radiating fins 105, or like features, extending from the central body and which may be adapted to aid a user in handling the device 10. A fluid passage 110 within the central body 100 may communicate with, and in the embodiment shown, be connected to, the inner portion 134 of the front cannula 130 and the inner portion 144 of the rear cannula 140, respectively, using adhesive, threaded interfaces, pressure fit, or other connection means. Alternatively, the central body 100 may be integrally formed with the front and/or rear cannulae 130 and 140. It is also appreciated that the front and/or rear cannulae may be transparent or translucent, in whole or part, to provide flash detection in alternative embodiments of the present invention. The fluid passage 110 may be defined by the opening within the central body between the front and rear cannulae when the cannulae are directly connected to the central body. The fluid passage 110 may be adapted to receive a sufficient amount of fluid to allow observation of the fluid (i.e., "flash") from outside the blood-drawing device 10. At the same time, the fluid passage 110 may have a sufficiently small volume so as to rapidly fill with fluid during the use of the blood-drawing device.

Preferably, the central body 100 may be constructed of plastic material suitable for medical use. Further, in the first embodiment of the present invention, all, or portions, of the central body 100 may be transparent, translucent, connected to transparent or translucent I.V. tubing, or otherwise adapted to permit detection of fluids passing through the central body and/or I.V. tubing from a vantage point outside of the blood-drawing device 10. For example, with particular reference to FIG. 1, the central body 100 may include a transparent wall that is adapted to permit the observation of "flash" when it occurs. In an alternate embodiment of the present invention, the side wall of the central body 100 also may be adapted to magnify or otherwise enhance the detection of fluid passing through the central body, although it is appreciated that a magnifying or enhancement feature is not necessarily required.

With particular reference to FIG. 2, the venting member 160 (i.e., a means for venting air) may be inserted over the rear cannula 140 and pressed against or near to the rear portion of the central body 100 (i.e., the portion proximate to the rear cannula 140). The venting member 160 may form a seal against the rear cannula that is sufficient to prevent blood from escaping past the venting member. In the first embodiment of the present invention, the venting member 160 may be gas, and particularly air, permeable, but at least partially impermeable to a liquid, such as blood. Preferably, the venting member 160 may be substantially porous for gas constituents less than about 5 microns in size, and substantially non-porous for liquid constituents about 5 microns or greater in size, however, it is appreciated that these approximate sizes should not be limiting for the invention. The venting member 160 may be constructed of any of a number of materials that provide the desired level of porosity, which may include, but are not limited to sintered, layered, rolled, foamed, perforated, or impregnated, hydrophyllic/hydrophobic compositions, porous polyethylene, porous polypropylene, porous polyfluorocarbon, absorbent paper, materials impregnated with dilute Russell Viper venom molded fiber, fiberglass, felt, granular starch, cellulose, polyacrylamide gel, hydrogel, a molded admixture of porous hydrophobic/hydrophyllic granules and sufficiently low density silicone, molded open cell polyurethane, and like polymeric materials. Examples of materials that may be used to construct the venting (i.e., porous) member 160 are discussed in U.S. Pat. No. 4,207,870 to Eldridge, and U.S. Pat. No. 4,340,068 to Kaufman, each of which are hereby incorporated by reference. The venting member 160 shown in FIG. 2 includes a base portion nearest the central body 100, a tapered portion furthest from the central body, and an annular recess in between the tapered portion and the central body. The tapered portion may facilitate the insertion of the flexible sleeve 150 over the venting member 160 and the annular recess may facilitate retention of the flexible sleeve after it is so inserted. It is also appreciated that the venting member 160 may have any shape in alternative embodiments, be it cylindrical, spherical, tapered, irregular, or other.

The rear cannula 140 may communicate with, and in the embodiment shown, extend out of, the central body 100, and through the venting member 160. The rear cannula 140 may terminate at a tapered or pointed end 142, which is adapted to be inserted into a fluid sample tube (shown in FIG. 4), or connected to a fluid collection reservoir. A flexible sleeve 150 may be disposed over and around the rear cannula 140. The flexible sleeve 150 may be stretched over the tapered portion on the end of the venting member 160, or in alternate embodiments, otherwise contact the venting member 160. The flexible sleeve 150 may be made of a shape memory material, such as elastic rubber or elastomeric silicone or latex, or the like, which will return to the shape shown in FIG. 2 as long as no other structure obstructs it. Examples of materials that may be used to construct the flexible sleeve 150 are discussed in U.S. Pat. No. 3,877,465 to Miyake, U.S. Pat. No. 5,086,780 to Schmitt, U.S. Pat. No. 6,110,160 to Farber, U.S. Pat. No. 6,533,760 to Leong, U.S. patent Pub. No. US 2002/0004647 A1 to Leong, and U.S. patent Pub. No. US 2003/0078544 A1 to Chen, each of which is hereby incorporated by reference. It is appreciated that any suitable material may be used for the flexible sleeve without departing from the intended scope of the present invention.

A generally cylindrical guide tube 116 may be connected to the threaded connector 112 by interlocking threads 114 and 120, respectively. When connected to the central body 100, the guide tube 116 may have an open end 118 adapted to receive a fluid sample container (shown in FIG. 4). The guide tube 116 may extend coaxially with the rear cannula 140 sufficiently beyond the tapered end 142 of the rear cannula to provide some degree of protection against inadvertent "needle sticks" by a user of the blood-drawing device 10 as well as to guide the reception of a fluid sample container.

The function of the first embodiment of the blood-drawing device 10 will now be described with reference to FIGS. 2-4. With reference to FIG. 2, the tapered end 132 of the front cannula 130 (or some extension thereof) may be inserted into a fluid containing body lumen prior to the insertion of a fluid sample container into the guide tube 116. In a preferred embodiment of the present invention, the front cannula 130 is inserted into a lumen containing a visually detectable fluid, such as blood. At the time that the front cannula 130 is inserted into the body lumen, it is assumed that the internal passages within the blood-drawing device (i.e., the passage through the front cannula 130, the fluid passage 110, the passage through the rear cannula 140, and the space inside the flexible sleeve 150) may be filled with atmospheric air or some other gas. When the front cannula 130 establishes communication with the fluid in the body lumen, fluid pressure in the lumen may force the fluid through the front cannula 130 towards the fluid passage 110.

Figure 3:
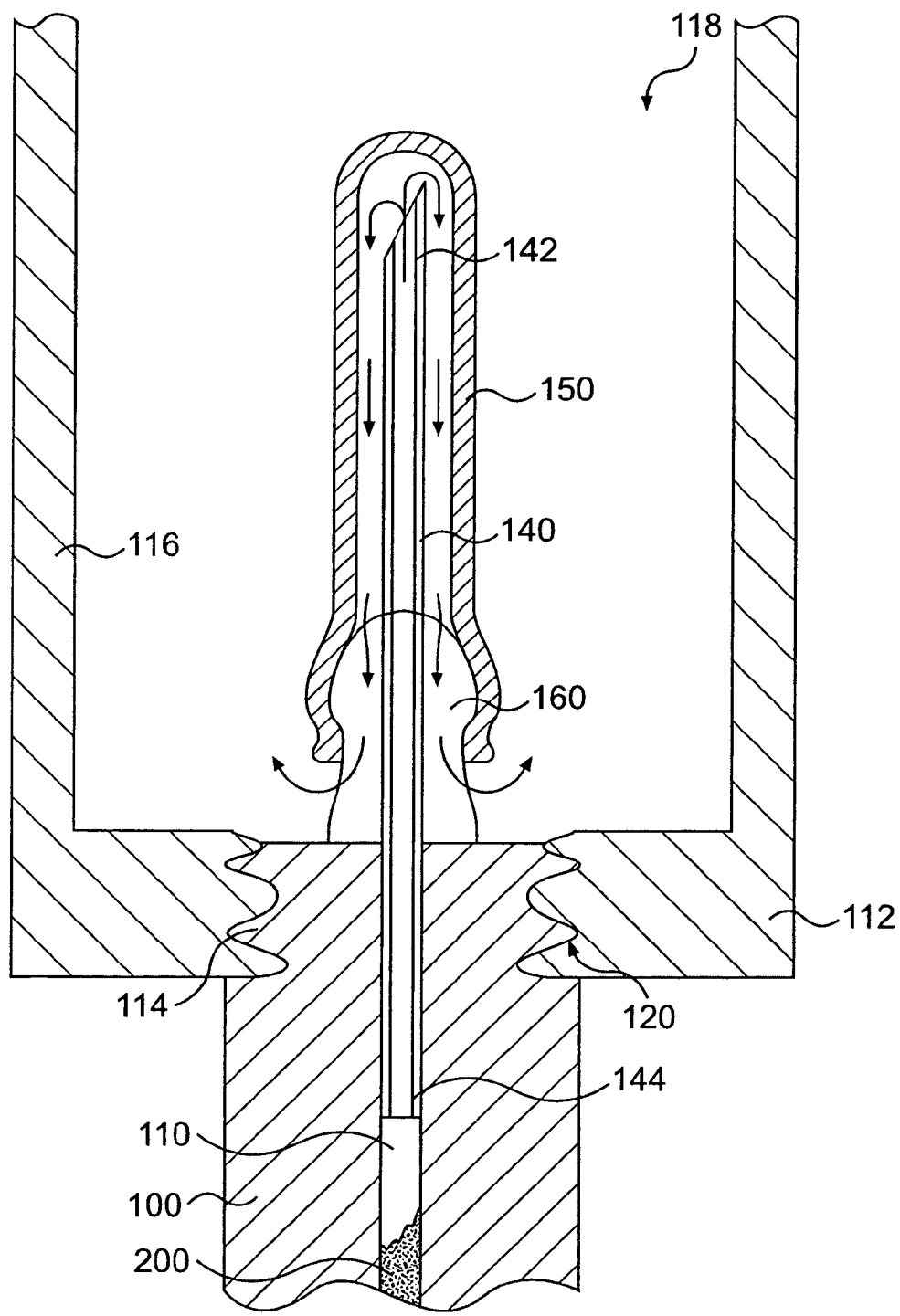
FIG. 3 is a side view in cross-section of the rear cannula portion of the first embodiment of the present invention.

With reference to FIG. 3, the flow of fluid 200 through the front cannula may begin to compress the air in the fluid passage 110, the rear cannula 140, and the space between the rear cannula and the flexible sleeve 150, driving the air towards the venting member 160. As blood flows into the device, all or a portion of the air in the device may flow through venting member 160 (i.e., be vented) because the venting member is gas permeable. As a result, there may be insufficient air pressure within the fluid passage 110 to resist the flow of the fluid 200 into the fluid passage 110, where it may be detected or observed as "flash" by a user. It is appreciated that "flash" may be detected at any point along the device that includes a transparent or translucent member, which may include, but not be limited to, a transparent or translucent cannula, central body, I.V. tubing, flexible sleeve, or other constituent member. After fluid fills the blood drawing device 10 and reaches the venting member 160, fluid leakage past the venting member may be prevented or reduced because the venting member may be at least partially impermeable to liquids, such as blood. As a result, the blood drawing device 10 may provide for detection of "flash" when the front cannula 130 is inserted into a body lumen (such as a vein) containing fluid (such as blood) to be withdrawn prior to the insertion of a fluid sample container into the guide tube 116 and the penetration of the rear cannula into the fluid sample container.

Figure 4:
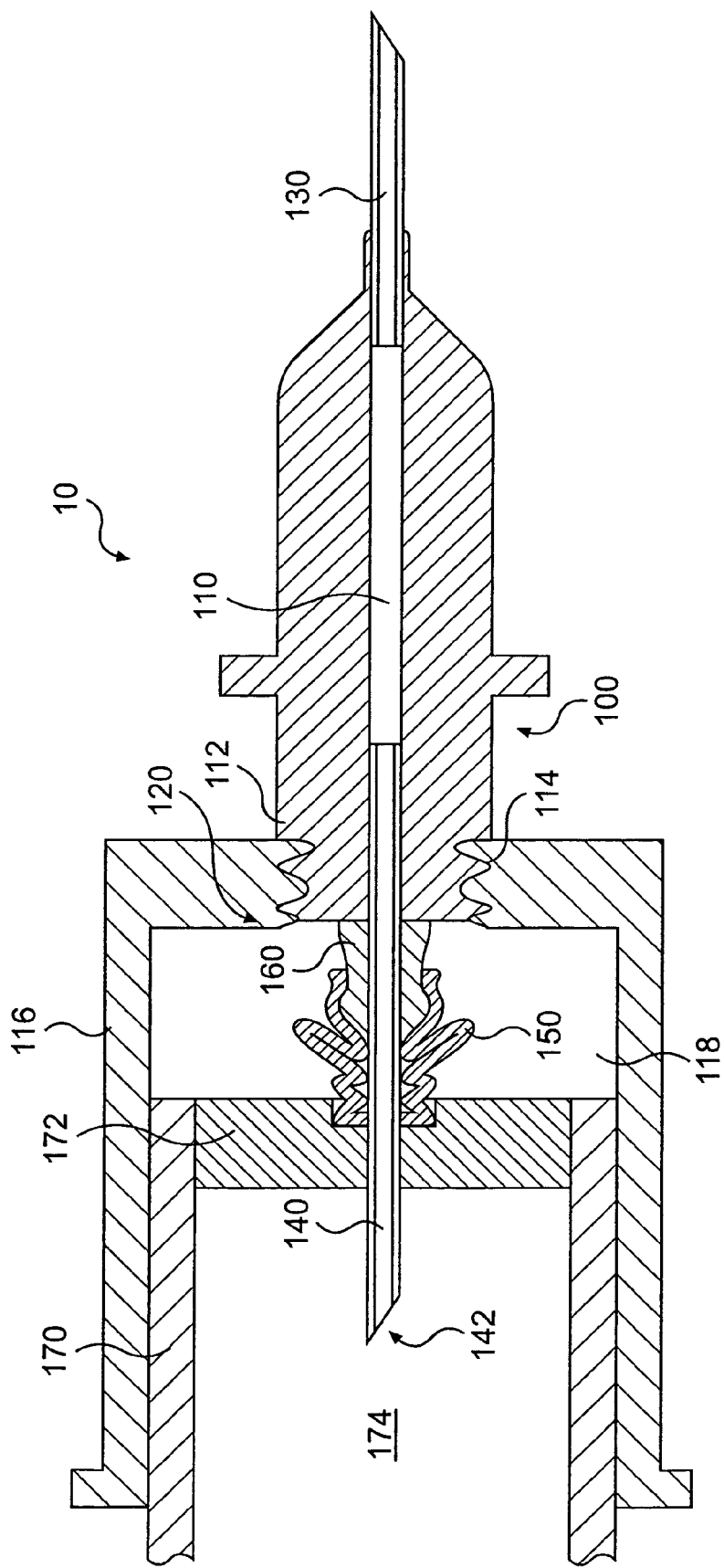
FIG. 4 is a side view in cross-section of the first embodiment of the present invention after the insertion of a sample collection tube.

With reference to FIG. 4, after the detection of "flash" within the fluid passage 110, a fluid sample container 170 may be used to collect a sample of the fluid flowing from the body lumen. The fluid sample container 170 may have a generally cylindrical outer wall, which is preferably, but not necessarily, transparent. The outer wall may define a collection chamber 174, which is preferably maintained in a vacuum condition prior to use of the container 170. A stopper 172 may be used to seal the open end of the container 170 so as to prevent air leakage into the collection chamber 174 prior to use of the container. One example of a commercially available vacuum container that may be used with various embodiments of the invention is a Vacutainer sold by Becton Dickinson & Co. of Franklin Lakes, N.J. Construction of vacuum containers, such as the one noted above, and the selection of materials therefore, are well known in the art.

In order to collect a fluid sample, the container 170 may be slid into the guide tube 116 through the opening 118 until it contacts the flexible sleeve 150. As the container 170 is pushed further into the guide tube 116, the tapered end 142 of the rear cannula presses into and pierces both the flexible sleeve 150 and the stopper 172. The flexible sleeve is pushed down towards, and may gather around, the venting member 160, as shown in FIG. 4. When the tapered end 142 of the rear cannula 140 is past the stopper 172, the pressurized fluid in the body lumen may readily flow through the blood-drawing device 10 to the vacuum space in the collection chamber 174.

After a first container 170 is full of fluid, it may be removed from the blood drawing device 10 for replacement by a second container. As the first container 170 is withdrawn from the guide tube 116, the flexible sleeve 150 may follow until it regains its original shape because it is constructed of shape memory material. The openings in the stopper 172 and the flexible sleeve 150, which were created by the rear cannula 140, may collapse or "heal" when the rear cannula is removed due to the nature of the material used to construct the stopper and the flexible sleeve. As a result, the fluid sample in the first container 170 may be sealed within it, and the fluid within the flexible sleeve 150 may be prevented from substantially leaking out of it. Thereafter, a second container 170 may be inserted into the guide tube 116 for collection of a fluid sample in the manner described above.

A second embodiment of the present invention is shown in an exploded side view in FIG. 5A. With reference to FIG. 5A, a Luer-type blood-drawing device is provided with a venting member 160. The central body 100 may be provided with an enlarged fluid passage 110 which may improve flash visibility. It is appreciated that the enlarged fluid passage could have any of a number of different shapes and sizes, which may be uniform or non-uniform over the length of the passage. It is further appreciated that the fluid passage 110 in each embodiment of the invention described herein, could have any of a variety of shapes and sizes without departing from the intended scope of the invention.

The butterfly needle 180 may be connected to the Luer-type hub 102 via a butterfly connection tube 182. The butterfly needle 180 may include a butterfly (i.e., front) cannula 184 and one or more wings 186. The butterfly cannula 184 may be inserted directly into the body lumen for blood collection. Flash may be observed in the transparent or translucent butterfly connection tube 182, in which case the central body 100 need not be transparent or translucent (although it could be).

With continued reference to FIG. 5A, known butterfly needles may use a butterfly connection tube 182 approximately 12 or more inches in length. This length of tubing is used so as to provide a sufficiently long column of air to permit flash observation when the blood-drawing device 10 is not provided with an air vent. Specifically, when a butterfly connection tube is used without an air vent, the flow of fluid through the butterfly needle may compress the volume of air in the butterfly connection tube 182, the fluid passage 110, the rear cannula 140, and the space between the rear cannula and the flexible sleeve 150. Because there is no vent provided, as blood flows into the device, the air in the device exerts an increasing level of backpressure on the blood, which may prevent blood flow and flash detection. The inclusion of a butterfly connection tube approximately 12 inches in length or greater increases the relative volume of air in the blood collection device. The increased volume of air in the device may permit flash detection before the air backpressure in the device rises to a level that prevents further blood flow into the device and could frustrate flash detection. Butterfly connection tubes of this length may be coiled in packaging, and retain some coil memory after they are removed from their packaging. Previously coiled butterfly connection tubes may resist being straightened for use and have an inherent bias towards returning to their coiled shape. Accordingly, manipulation of a butterfly needle attached to a previously coiled butterfly connection tube may be difficult due to the connection tube's tendency to recoil. This action can be the cause of accidental needle sticks for the healthcare worker and the patient. Furthermore, the coil memory of the tubing may make handling generally difficult for lumen insertion, and/or maintenance of the needle in the lumen.

The butterfly connection tube 182 used in the device shown in FIG. 5A may be less than approximately 12 inches in length, and more preferably, may be only a few inches in length as a result of the inclusion of a venting member 160 in the blood-drawing device 10. The inclusion of the venting member 160 may obviate the need for a relatively long column of air in the butterfly connection tube that otherwise may be needed to indicate flash. The use of a shortened butterfly connection tube 182 may also obviate the need to coil the tube prior to use, thereby eliminating the issues associated with coil memory in the tube, as well as make it possible to use rigid or semi-rigid connection tubes that may better enable placement of the front cannula into the body lumen.

Figure 13:
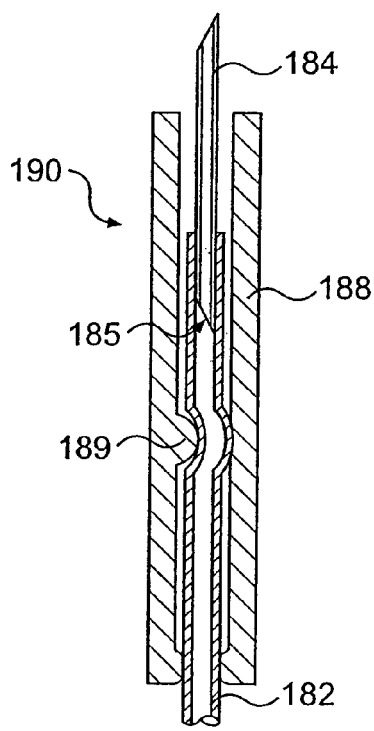
FIG. 13 is a side view in cross-section of a blood flow control mechanism that may be used with various embodiments of the present invention and/or independently in accordance with an eighth embodiment of the invention.

With reference to FIG. 13, a butterfly needle 180, such as shown in FIG. 5A, may optionally be provided with a blood flow control member 190. The blood flow control member 190 may include a slideable control valve 188 surrounding the distal end of the butterfly connection tube 182 and the butterfly cannula 184. The slideable control valve 188 may include an inner convex boss 189 adapted to restrict flow through the butterfly cannula 184 when positioned near the inner butterfly cannula end 185. Flow through the butterfly cannula 184 may be controlled by manually sliding the control valve 188 so that the inner convex boss 189 is nearer to or more removed from the inner butterfly cannula end 185. The slideable control valve 188 may completely or partially shield the distal end of the butterfly cannula 184 when it is positioned to block or restrict flow through the butterfly cannula. Control over blood flow through the butterfly cannula 184 may be used to avoid collapsing small or low pressure lumens (typical of children and the elderly) during negative pressure conditions experience during blood drawing procedures. It is appreciated that the blood flow control member 190 could optionally be used with other embodiments of the present invention that do not incorporate a butterfly needle. It is also appreciated that the flow control member 190 may be used with any conventional I.V. infusion or fluid drawing device. It is further appreciated that alternative control valve 188 designs are known in the art and may be substituted for the afore-described design without departing from the intended scope of the present invention.

It is further appreciated that in an alternative embodiment of the present invention shown in FIG. 5A, the butterfly needle 180 may be modified to eliminate the butterfly wings 186 without departing from the intended scope of the invention. More specifically, the embodiment shown in FIG. 5A could be modified so that the butterfly cannula 184 is replaced by a conventional front cannula, which may be connected to the central body 100 by any elements, including but not limited to a flexible tube, rigid tube, or semi-rigid tube, any one of which may be constructed of transparent or translucent material to indicate flash.

A variation of the embodiment of the present invention shown in FIG. 5A is shown in FIG. 5B, in which the butterfly needle 180 is replaced by a front cannula 130 connected directly to the Luer-type hub 102. The Luer-type hub 102 is adapted to connect to the Luer-type central body 100 in accordance with known methods.

A third embodiment of the present invention is shown in FIG. 6. With reference to FIG. 6, a porous member 160 may be inserted over the rear cannula 140 and slightly separated from the rear portion of the central body 100 (i.e., the portion proximate to the rear cannula 140), leaving a small space 161 between the central body and the porous member. The porous member 160, itself, and/or the seal it forms against the rear cannula, may not completely prevent blood from escaping past the porous member. In such instances, the porous member 160 may be constructed of material that is porous to gas (air) and somewhat, but not perfectly, non-porous to blood.

The porous member 160 may preferably include a tapered portion, however, it is appreciated that the porous member may have any alternative shape, such as cylindrical, spherical, irregular, or the like, without departing from the intended scope of the invention.

In embodiments in which the porous member 160 is not completely non-porous to blood, a gas or air porous and/or liquid absorbent spacer 168 may be inserted behind the porous member 160 in the space 161. The porous spacer 168 may be constructed of any of a number of materials that are porous to gas (air), and partially, substantially, or completely non-porous to liquids such as blood, and/or partially or completely absorbent of such liquids. For example, the porous spacer 168 may be constructed of sintered, layered, rolled, foamed, perforated, or impregnated hydrophyllic/hydrophobic compositions, porous polyethylene, porous polypropylene, absorbent paper, molded fiber fiberglass, felt, granular starch, cellulose, polyacrylamide gel, hydrogel, or the like. It is appreciated that in some embodiments the porous spacer 168 may permit some blood seepage past it, however, it is expected that the porous spacer may reduce or slow such seepage. After the porous spacer 168 is positioned in the air space 161, the flexible sleeve 150 may be stretched over the porous member 160 and a portion, or none, of the porous spacer 168, so long as at least of portion of the porous spacer remains in communication with the ambient.

A fourth embodiment of the present invention is shown in FIG. 7. With reference to FIG. 7, a rear cannula 140, non-porous member 162, and air space 161 arrangement, similar to that shown in FIG. 6, are used. The flexible sleeve 150 is modified from that shown in earlier embodiments to include a side tubulation 154 and a porous insert 152. The porous insert 152 may be any size and may be constructed of sintered polyethylene, perforated plastic, porous fiber, rolled fiber, or the like. It is appreciated that in some embodiments the porous insert 152 may permit some blood seepage past it, however, it is expected that the porous insert may reduce or slow such seepage. As a result of the inclusion of the porous insert 152 between the interior of the sleeve 150 and the ambient, air in the blood-drawing device 10 may vent from the interior of the sleeve through the porous insert 152 when the device is used to draw blood. Blood within the sleeve 150 may be prevented however, at least initially, from passing the porous insert 152.

Figure 10:
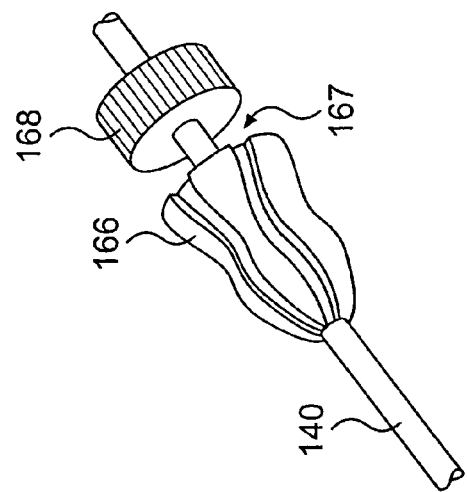
FIG. 10 is a pictorial view of the venting member and porous spacer shown in FIG. 8.
Figure 8:
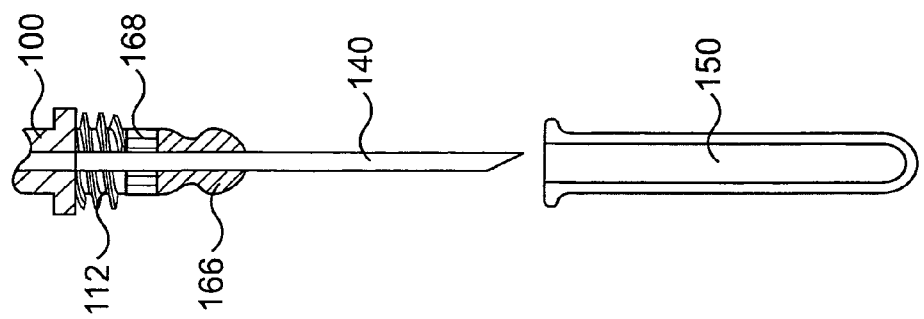
FIG. 8 is a side view in cross-section of the rear cannula portion of a fifth embodiment of the present invention.

A fifth embodiment of the present invention is shown in FIGS. 8 and 10. With reference to FIGS. 8 and 10, a non-porous venting member 166 may be inserted over the rear cannula 140 and slightly separated from the rear portion of the central body 100 (i.e., the portion proximate to the rear cannula 140), by a porous spacer 168 between the central body and the non-porous venting member. The non-porous venting member 166 may form a seal against the rear cannula that is sufficient to prevent blood from escaping past the non-porous venting member along its surface in contact with the rear cannula. The non-porous venting member 166 may be constructed of material, such as plastic suitable for medical use, which is non-porous to both gas (air) and blood. The outer surface of the non-porous venting member 166 may include one or more grooves, channels, bumps, or like features 167 (collectively "venting features 167") that permit the passage of air. It is appreciated that the venting features 167 may be very small (of a size capable of permitting the passage of air molecules). Such small venting features may inherently restrict the passage of blood molecules, which typically may be larger that air molecules. The non-porous venting member 166 may preferably have a tapered tip and adapted to receive a flexible sleeve 150 stretched over it.

A porous spacer 168 may be inserted between the non-porous venting member 166 and the central body 100. The porous spacer may be constructed of any of a number of materials that are porous to gas (air), and partially, substantially, or completely non-porous to liquids such as blood. For example, the porous spacer 168 may be constructed of sintered polyethylene, perforated plastic, porous fiber, rolled fiber, or the like. It is appreciated that in some embodiments the porous spacer 168 may permit some blood seepage past it, however, it is expected that the porous spacer may reduce or slow such seepage.

With continued reference to FIGS. 8 and 10, the flexible sleeve 150 may be stretched over the non-porous venting collar 166 and at least a portion of the porous spacer 168 such that at least of portion of the porous spacer remains in direct communication with the ambient. Air in the blood drawing device may vent from the interior of the sleeve 150 past the venting features 167 on the non-porous venting member 166 and through the porous spacer 168 to the ambient when the device is used to draw blood. Blood within the sleeve 150 may be prevented however, at least initially, from passing the porous spacer 168 as a result of the nature of the material in the porous spacer and the relatively small passageways provided by the venting features 167.

Figure 9:
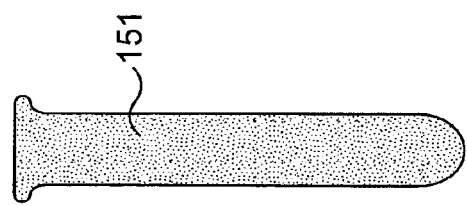
FIG. 9 is a side view of a flexible sleeve constructed in accordance with a sixth embodiment of the present invention.

A sixth embodiment of the present invention is shown in FIG. 9. With reference to FIG. 9, an air-permeable, completely or partially blood-impermeable flexible sleeve 151 is provided. The air-permeable sleeve 151 may be used in conjunction with or independently of the above-referenced embodiments of the present invention. A known flexible sleeve is described in U.S. Pat. No. 3,877,465 to Miyake, incorporated by reference above. In the present embodiment of the invention, the elastic sheath material making up the wall of the sleeve 151 may be constructed of a material that is largely air-permeable, but partially, largely or entirely impermeable to blood. The air-permeable sleeve 151 may be used to isolate the rear cannula 140 of a blood drawing device from the ambient in the same manner as conventional sleeve may isolate rear cannulae. During a blood drawing procedure using a device not equipped with a means for venting air from the sleeve, blood from a lumen may be slowed or prevented from entering the device due to air back pressure in the device. In these devices the air in the device may be trapped because there is no vent provided. In the present embodiment, an air-permeable sleeve 151 replaces a conventional sleeve on the blood drawing device. The air-permeable sleeve 151 may provide a pathway to vent air from the device interior, through the sleeve wall, to the ambient. As the air is vented, the blood filling the device may contact the air-permeable sleeve 151. However, the air-permeable sleeve 151 may prevent or retard the flow of blood through its wall because the pore size of the air-permeable sleeve may be large enough to allow the passage of air, but too small to allow much or any blood to pass. This air passage-blood blockage may permit blood to fill the needle and/or the sleeve 151 more readily because there is reduced or no air back pressure inhibiting the flow of blood into the blood drawing device. As a result, a blood drawing device equipped with the air-permeable sleeve 151 may indicate flash (the visual indication of blood flow into the needle) more readily. The air-permeable sleeve 151 may be used with conventional needle drawing or infusion sets (such as butterfly needles), hypodermic needles, or the like, to enhance flash indication.

The air-permeable sleeve 151 may be made of any suitable material that is completely or at least partially air-permeable and substantially blood impermeable, such as for example, low density polyethylene or low density rubber. One example of a method of making such material is described in U.S. Pat. No. 5,641,442. A second example may be made of crumbed material of sufficiently low density/high flexibility to allow the required flexibility in spite of the use of thermal binders like polyethylene. Low density material such as low density silicone may be sifted using a #80 mesh and mixed with #100 mesh low density polyethylene. This mixture may be heated at approximately 280° F. and injected into a cavity mold to form the selectively porous sleeve 151.

An air-permeable sleeve may be constructed of porous material formed from the combination of a hydrophobic porous material with a hydrophilic porous agent. The hydrophobic porous material, for example, may be a polymeric matrix of either thermoplastic resins such as polyvinyl chloride or copolymers thereof, or synthetic or natural thermosetting rubber-like polymers. In a second example, the polymeric matrix may be rubber-like polymers combined with additives such as anti-degradants, cross-linking agents, cure inhibitors, platinum and other type catalysts, inert fillers, or like materials used to compound thermosetting compounds, and intimately mixed with a hydrophilic porous agent such as silica hydrogel, precipitated hydrated silica, for example such as that sold under the trademark Hi-Sil from PPG Industries, or polyacrylamide gel, cross-linked homopolymer of acrylamide, for example such as that sold under the trademark Agrosoake from Agrosoake International, inert fillers and/or water or solvent soluble porosics. In a third example, the polymeric matrix may be made of a synthetic or natural thermosetting polymer or copolymer, such as those that may be made in accordance with the methods disclosed in U.S. Pat. No. 4,548,835 to Takahashi, et al. and U.S. Pat. No. 4,153,760 to Sundberg et al, for example, each of which is hereby incorporated by reference.

The porous agent may be prepared by polymerizing acrylamide in the presence of an aqueous sodium carbonate to produce a partially hydrolyzed, lightly cross-linked, polyacrylamide gel in accordance with the method disclosed in U.S. Pat. No. 3,022,279 to Proffitt, for example, which is hereby incorporated by reference. The polyacrylamide gel may be produced in bead or granular form using an inverse suspension polymerization method for water-soluble monomer, which is disclosed in U.S. Pat. No. 2,982,749 to Friedrich et al., for example, and which is hereby incorporated by reference.

In one embodiment, for example, the hydrophilic granules may be added to the hydrophobic material in sufficient quantities to create a hydrophilic/hydrophobic porous material. The porosity of the hydrophobic material may be manifested by a network of voids/pores extending throughout the matrix or binder, between neighboring particles of the dispersed filler and portions of the polymeric matrix, which may be achieved by the shrinking of the swollen hydrophilic granules during the dehydration/curing phase. The resultant degree of porosity may be controlled by the amount of water or water substitute added to the polymeric matrix binder material during the mixing phase, the vulcanization of the polymeric matrix (such as for example, under hydrostatic conditions in a steam autoclave to a state of cure using the pressurized steam as a source of heat), the proportion and size of the hydrophilic granules added, the duration of the mixing phase, and the wall thickness of the elastomeric sleeve. The hydrophilic granules may be mixed with a normally hydrophobic binder (and water or a water substitute may be added to control porosity) in a mixing type extruder.

When this material is formed into an air-permeable flexible sleeve 151, water-based liquids such as blood may rapidly soak into the pores/voids containing the granular material, causing the granules to swell and seal the pores/voids contained within the polymeric matrix. Thus, the air-permeable flexible sleeve, which is initially permeable to air, may become relatively impermeable to liquids, such as blood, due to the swelling of the moisture reactive granules entrapped within the pores/voids within the polymeric matrix.

Figure 11:
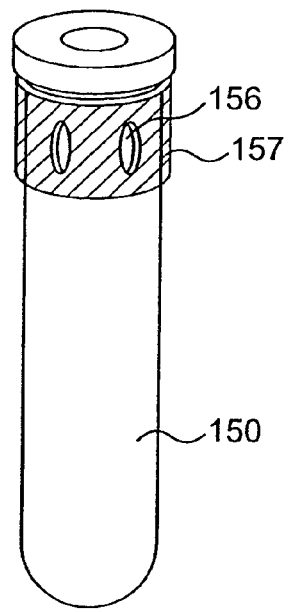
FIG. 11 is a pictorial view of a seventh embodiment of the present invention.
Figure 12:
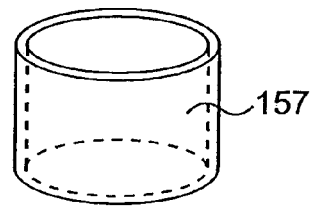
FIG. 12 is a pictorial view of the porous collar shown in FIG. 11.

A seventh embodiment of the present invention is shown in FIGS. 11 and 12. With reference to FIGS. 11 and 12, a flexible sleeve 150 may be provided with one or more openings or perforations 156 extending through the wall of the sleeve. The openings 156 may be relatively small, only needing to be capable of permitting the passage of air molecules. A porous collar 157 constructed of sintered polyethylene, perforated plastic, porous fiber, rolled fiber, or the like, may be provided over the openings 156. The flexible sleeve 150 may be stretched over the non-porous member inserted over the rear cannula, (such as non-porous member 162 shown in FIG. 7). Air in the blood drawing device may vent from the interior of the sleeve 150 past the openings 156 in the flexible sleeve wall and through the porous collar 157 to the ambient when the device is used to draw blood. Blood within the sleeve 150 is prevented however, at least initially, from passing the porous collar 157 as a result of the nature of the material making up the porous collar and potentially by the relatively small passageways provided by the openings 156.

Figure 14:
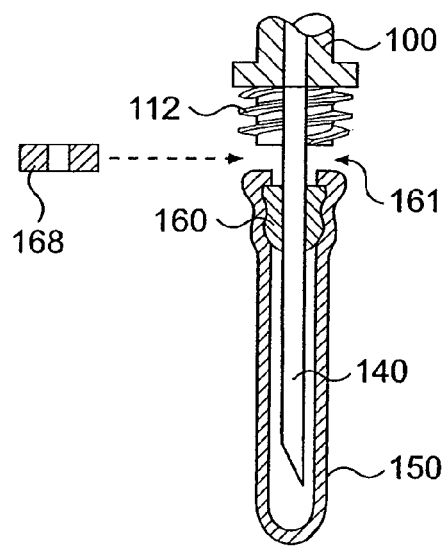
FIG. 14 is a side view in cross-section of a rear cannula portion of a ninth embodiment of the present invention.

An alternative embodiment of the present invention is shown in FIG. 14, in which the venting member 160 is spaced from the central body 100 and the flexible sleeve 150 envelopes the entire side wall of the venting member. A portion of the base end wall of the venting member 160 is exposed to the ambient to permit air to vent. In a further alternative, a porous spacer 168 may be disposed in the air space 161 to block or absorb any blood seepage past the venting member.

Each of the embodiments of the present invention shown in all of the afore-noted figures may also utilize a transparent or translucent flexible sleeve 150 to provide flash detection. An example of a transparent sleeve is disclosed in U.S. Pat. No. 3,886,930 to Ryan, which is hereby incorporated by reference. Use of a transparent or translucent sleeve 150 may make it unnecessary for the central body 100 or other elements of the device to be constructed of transparent or translucent material because the flash may be detected through the wall of the sleeve itself and thereby allow for the retrofitting of known blood-drawing devices to provide air venting and flash detection without other modification of the device. Use of a transparent or translucent sleeve 150 may also obviate the need to have discreet front and rear cannulae 130 and 140. The front and rear cannulae may be constructed from a single integral piece of material because in this embodiment of the invention there may be no need to view flash in the central body 100.

Each of the embodiments of the invention described above may also be modified such that the porous member 160 (FIGS. 1-6), the porous collar 157 (FIGS. 11-12), the porous insert 152 (FIG. 7), or the porous spacer 168 (FIGS. 6, 8 and 10) includes or is constructed of any one or more of a number of substances that may permit air venting, and limit and reduce blood seepage, but not completely prevent blood seepage through the particular porous structure. Such materials include absorbent pleated or rolled paper, molded fiber or fiberglass, felt, sintered compositions of hydrophilic/hydrophobic materials such as polyethylene and polyacrylamide gel, and/or any other material capable of venting air but impeding the passage of liquids.

For example, hydrophilic and/or hydrophobic substances such as polyethylene and granular starch, cellulose, polyacrylamide gel, or the like may be used. Such substances are known in the art, and may be used to permit gas (e.g., air) to flow through them, but absorb or block liquid substances. Accordingly, a porous member, collar, insert, or spacer, comprised of these materials may be used to permit the air in a blood drawing device to vent past it until it is contacted by a liquid, such as blood, at which time the blood may be absorbed.

Similarly, glass powder or fiber may be used to simulate clotting, or a clotting agent, such as dilute Russell Viper Venom, may be used to permit air venting with little or reduced blood seepage. Russell Viper Venom is known in the art as a clotting agent. A porous member, collar, insert, or spacer impregnated with a clotting agent or simulating clotting agent may be used to permit the air in a blood drawing device to vent until it is contacted by blood, at which time the blood may clot or act as clotted and reduce further blood seepage through the porous member, collar, insert or spacer. As a result, use of hydrophilic and/or clotting agents in the previously described porous member, collar, insert, or spacer may permit improved blood flow into a blood drawing device and flash detection.

A multitude of different means for venting air are described above. It is appreciated that various embodiments of the invention may include any type of means for venting air disposed between a flexible sleeve covering the rear cannula of a blood drawing device and an ambient, including, but not limited to one or more air porous materials provided individually or in combination, and/or combinations of air porous and non-air porous materials.

It will be apparent to those skilled in the art that variations and modifications of the present invention can be made without departing from the scope or spirit of the invention. For example, the shape, size, and material selection for the various components of the blood-drawing device may be changed without departing from the intended scope of the invention and appended claims. It is further appreciated that forming one or more elements of the apparatus embodiments of the present invention integrally as opposed to separately is intended to fall within the scope of the invention and appended claims.

What is claimed is:

1. A flexible sleeve configured to receive a cannula of a blood drawing device located outside of a patient body, said sleeve comprising: an open end, a closed end, and an air-permeable blood-impermeable portion, wherein at least a part of said air-permeable blood-impermeable portion is provided near the sleeve open end, and wherein the sleeve open end comprises elastic material adapted to be fit over a portion of the blood drawing device, and wherein the air-permeable blood-impermeable portion comprises:

one or more openings provided in non-porous flexible sleeve material; and a porous collar covering the one or more openings in the non-porous flexible sleeve material.

2. A flexible sleeve configured to receive a cannula of a blood drawing device located outside of a patient body, said sleeve comprising: an open end, a closed end, and an air-permeable blood-impermeable portion, wherein at least a part of said air-permeable blood-impermeable portion is provided near the sleeve open end, and wherein the sleeve open end comprises elastic material adapted to be fit over a portion of the blood drawing device, and wherein the air-permeable blood-impermeable portion comprises:

a tubulation provided in non-porous flexible sleeve material; and a porous insert disposed in the tubulation.

3. A sleeve configured to receive a cannula of a blood drawing device located outside of a patient body, said sleeve comprising: an open end, a closed end, and an air-permeable blood-impermeable portion, wherein the sleeve open end is adapted to be fit over a portion of the blood drawing device, and wherein the air-permeable blood-impermeable portion comprises:

one or more openings provided in non-porous flexible sleeve material; and a porous collar covering the one or more openings in the non-porous flexible sleeve material.

4. A sleeve configured to receive a cannula of a blood drawing device located outside of a patient body, said sleeve comprising: an open end, a closed end, and an air-permeable blood-impermeable portion, wherein the sleeve open end comprises is adapted to be fit over a portion of the blood drawing device, and wherein the air-permeable blood-impermeable portion comprises:

a tubulation provided in non-porous flexible sleeve material; and a porous insert disposed in the tubulation.

* * * * *